United States Patent [19]

Koch

[11] 4,352,794
[45] Oct. 5, 1982

[54] BETA-CYCLODEXTRIN AS ANTI-ACNE AGENT

[76] Inventor: Jürgen Koch, Buchenalle 7c., Hamburg 54, Fed. Rep. of Germany

[21] Appl. No.: 211,232

[22] Filed: Nov. 28, 1980

[30] Foreign Application Priority Data

Nov. 27, 1979 [DE] Fed. Rep. of Germany ....... 2947742

[51] Int. Cl.³ ............................................. A61K 31/715
[52] U.S. Cl. .............................. 424/180; 424/DIG. 4; 424/69; 424/340; 424/361; 536/103
[58] Field of Search ................ 536/103; 424/180, 361, 424/DIG. 4

[56] References Cited

U.S. PATENT DOCUMENTS 3,821,192 6/1974 Montgomery et al. ............ 536/103
4,228,160 10/1980 Szejtli et al. ........................ 536/103
4,267,166 5/1981 Yajima ................................ 424/361

OTHER PUBLICATIONS

"Die Starke", 29, 1977, No. 1, pp. 26-33.

Primary Examiner—Johnnie R. Brown
Attorney, Agent, or Firm—Fleit & Jacobson

[57] ABSTRACT

A method for treating acne in which beta-cyclodextrin is applied to the acne typically in the form of a lotion, ointment, cream, gel or the like, in a concentration from 0.1-10, preferably 1-5%, by weight.

8 Claims, No Drawings

BETA-CYCLODEXTRIN AS ANTI-ACNE AGENT

The present invention relates to the use of beta-cyclodextrin for the treatment of acne.

Acne is a disease of the sebaceous glands. It is of extremely frequent occurrence, particularly if one also counts its early stages, which are often indicated as "skin impurities".

The initial stage of acne is characterized by the accumulation of keratinous sebum plugs in the openings of the sebaceous glands and the formation of comedones; afterwards, also inflammatory changes occur, the different manifestations of which are especially determined by the deepness and degree of the damage to the skin tissue. This may finally result in cicatrization and/or epithelium growth and the formation of cysts.

Depending on the degree of severity and pronounced appearance, one speaks of Acne vulgaris, Acne comedonica, Acne papulo pustulosa, Acne conglobata, etc.

Although the causes of these changes of the skin have not yet been completely elucidated, a great many proposals have been made for the cosmetic and therapeutical treatment of acne. This is mainly due to the fact that acne particularly occurs on the skin of the face, chest and back, which by most patients, also on psychological grounds, is experienced as particularly unpleasant. The fact that acne occurs most frequently in the period of puberty leads to the presumption that hormones play a part in the process, and it has been suggested to treat acne with, e.g., estrogenic hormones. However, also bactericides, antibiotics and keratolytic agents are used. These agents, however, while mostly having an insignificant anti-acne activity partly cause considerable side effects, such as irritation of the skin, toxicity and hormonal changes.

It is therefore an object of the invention to provide an active substance that does not have these drawbacks and shows a distinct activity against acne. According to the invention, it has been found that beta-cyclodextrin fulfills these requirements. Clinical tests have shown that within a short period of time a considerable symptomatic healing is obtained of acne in all its different manifestations when treated with beta-cyclodextrin.

The invention therefore relates to the use of beta-cyclodextrin as anti-acne agents in cosmetical and pharmaceutical preparations for the treatment of acne.

Beta-cyclodextrin, also known, inter alia, as "Schardinger Dextrin" or cycloheptaamylose, is obtained by the fractionation of enzymatically decomposed starch. In "Die Stärke", 29, 1977, No. 1. pp. 26–33, a number of possibilities are discussed for the use of cyclodextrin in the pharmaceutical industry, in which the cyclodextrins can be advantageous because of their capability of forming inclusion compounds, to increase the solubility of poorly soluble medicine, to improve the stability of other compounds or to reduce the volatility of other compounds. However, any use of beta-cyclodextrin per se as a pharmaceutically active substance is not described in this publication. On account of its capability to form inclusion compounds, beta-cyclodextrin has already been proposed for use in deodorizing cosmetic preparations (JA-PS No. 41440/78), as well as in bath additives (JA-PS No. 63126/75).

However, from the prior art it is not known so far that beta-cyclodextrin is an active agent for treating acne. Since the activity is presumably of a purely physical nature, the use of beta-cyclodextrin does not cause any significant, undesirable side effects on the skin or skin flora, as is the case with chemically or physiologically active substances.

The beta-cyclodextrin can be used in any form of application. Typical examples are lotions, ointments, creams, gels, etc. In general, the beta-cyclodextrin content in these applications is from 0.1–10, preferably 1–5% by weight.

Preferably, the medication contains a mixture of beta-cyclodextrin with one or more carriers in which the mixture contains no organic substances with a molecular weight between 100 and 10,000 daltons other than at most 1 percent of a preserving agent. The carrier is preferably a mixture of ethanol and water, most preferably with a preserving agent, or ethylene glycol, most preferably also with water and/or a preserving agent. Solid powdered carriers such as talcum or polymer thickeners over 10,000 daltons also can be used. The range of 100 to 10,000 daltons includes carriers such as fats, oils, waxes, perfumes, etc., which are conventional liquid carriers and additives used for beta-cyclodextrin in pharmaceutical or cosmetic compositions and which tend to form clathrates thereby inactivating the cyclodextrin.

The invention will now be further illustrated with reference to the following test results:

Two aqueous-alcoholic solutions of the following compositions were used for the treatment of 64 acne cases:

| Preparation | A | B |
|---|---|---|
| Beta-cyclodextrin | 10 g | 1 g |
| Alcohol 410 (undenatured ethanol 95%) | 300 g | 300 g |
| Preserving agent (Irgasan DP 300 [CIBA-Geigy] = 2,4,4'-trichloro-2-hydroxydiphenylether | 0.5 g | 0.5 g |
| Demineralized H$_2$O to | 1000 g | 1000 g |

All varieties of Acne vulgaris, Acne comedonica, Acne papulo pustulosa, Acne conglobata, single pustules, etc. were treated, i.e., acne cases occuring in puberty as well as those occurring afterwards, with patients of both sexes; in all these cases the disease had already existed for several years.

The treatment comprised of twice-daily treatment of the parts of the body affected by acne, and in weekly intervals the number of the remaining pustules and blackheads was recorded and plotted against the starting number. Among the 54 cases of acne in all its different manifestations and degree of severity treated with Preparation A, a symptomatic healing of 60–100% was observed after 1–4 weeks with 43 cases tested (i.e., 80%). With Preparation B, and in an experiment with 10 persons, an insignificant improvement was obtained in 3 cases.

I claim:

1. A method of treating a patient suffering from acne, comprising topically applying to the acne beta-cyclodextrin in an acne treating effective amount, the beta-cyclodextrin being applied to the acne in a cosmetic or pharmaceutical acceptable carrier, the carrier containing substantially no organic compounds with molecular weights between 100 and 10,000 daltons.

2. The method of claim 1 in which the carrier contains no organic substances with a molecular weight between 100 and 10,000 daltons.

3. The method of claim 1 in which the concentration of the beta-cyclodextrin in the carrier is from 0.1 to 10% by weight.

4. The method of claim 1 in which the concentration of the beta-cyclodextrin in the carrier is from 1 to 5% by weight.

5. The method of claim 1 in which the beta-cyclodextrin is applied to the acne in the form of a lotion, ointment, cream or gel.

6. The method of claim 1 in which the beta-cyclodextrin is applied to the acne in the form of an aqueous-alcoholic solution.

7. The method of claim 1 in which the carrier contains a preserving agent.

8. The method of claim 1 in which the carrier contains at most 1% of a preserving agent.

* * * * *